US010436764B2

(12) United States Patent
Dinu et al.

(10) Patent No.: US 10,436,764 B2
(45) Date of Patent: Oct. 8, 2019

(54) SYSTEM AND METHOD FOR PLANT FUEL QUALITY

(71) Applicant: General Electric Company, Schenectady, NY (US)

(72) Inventors: Constantin Dinu, Greenville, SC (US); Otman Dinari, Greenville, SC (US); Michal Knapczyk, Warsaw (PL)

(73) Assignee: General Electric Company, Schenectady, NY (US)

( * ) Notice: Subject to any disclaimer, the term of this patent is extended or adjusted under 35 U.S.C. 154(b) by 213 days.

(21) Appl. No.: 15/385,457

(22) Filed: Dec. 20, 2016

(65) Prior Publication Data
US 2018/0172658 A1 Jun. 21, 2018

(51) Int. Cl.
| | |
|---|---|
| *G01N 33/22* | (2006.01) |
| *F02C 7/22* | (2006.01) |
| *G01N 33/18* | (2006.01) |
| *G01N 33/28* | (2006.01) |

(52) U.S. Cl.
CPC .............. *G01N 33/22* (2013.01); *F02C 7/22* (2013.01); *G01N 33/18* (2013.01); *G01N 33/2888* (2013.01)

(58) Field of Classification Search
CPC .......... F02C 7/22; G01N 33/22; G01N 33/18; G01N 33/2888
See application file for complete search history.

(56) References Cited

U.S. PATENT DOCUMENTS

| | | | | |
|---|---|---|---|---|
| 4,515,007 | A * | 5/1985 | Herman | G01M 3/20 55/DIG. 9 |
| 4,519,415 | A * | 5/1985 | Carn | F17C 3/022 137/318 |
| 5,201,435 | A * | 4/1993 | Harding | B65D 90/24 220/567.2 |
| 5,360,738 | A * | 11/1994 | Jones | E21B 21/08 250/255 |
| 6,034,282 | A | 3/2000 | Dyckman et al. | |

(Continued)

FOREIGN PATENT DOCUMENTS

| | | |
|---|---|---|
| AU | 2012100395 A4 | 5/2012 |
| EP | 1 906 179 A1 | 4/2008 |

(Continued)

OTHER PUBLICATIONS

Brummel, H.G., On-Line Monitoring of Power Plants, Siemens Power Generation (PG), pp. 1-13 (Jan. 2006).

(Continued)

*Primary Examiner* — David A Rogers
(74) *Attorney, Agent, or Firm* — Fletcher Yoder, P.C.

(57) ABSTRACT

A plant-integrated measurement and monitoring system includes one or more sampling ports disposed throughout to provide fuel samples at key locations in the plant. Additional sampling ports are included to provide samples of water, lube oil or other fluids. Each fuel sample is analyzed in an automated analyzer that determines a presence of contaminants. Results of the analysis are interpreted by the plant control system to determine quality attributes of the fuel samples and identify locations and/or causes of identified anomalies. The control system further issues alerts or actions to limit an impact of the identified anomalies.

19 Claims, 5 Drawing Sheets

(56) References Cited

U.S. PATENT DOCUMENTS

| | | | |
|---|---|---|---|
| 6,318,581 B1* | 11/2001 | Garton | B65D 90/24 220/4.12 |
| 6,675,641 B2 | 1/2004 | Gehner et al. | |
| 6,859,517 B2 | 2/2005 | Wilson et al. | |
| 7,927,883 B2 | 4/2011 | Tuli et al. | |
| 8,055,322 B2 | 11/2011 | Ye | |
| 8,152,896 B2 | 4/2012 | Elledge et al. | |
| 8,276,780 B2* | 10/2012 | Oltman | F16L 5/08 220/4.12 |
| 8,663,996 B2* | 3/2014 | Beeson | G01N 27/16 422/105 |
| 9,329,102 B2 | 5/2016 | Hwang et al. | |
| 9,354,220 B2 | 5/2016 | Rebinsky | |
| 10,017,399 B2* | 7/2018 | Kamen | E04H 1/1205 |
| 2002/0112481 A1 | 8/2002 | Whitehead et al. | |
| 2006/0252975 A1 | 11/2006 | Zakoshansky et al. | |
| 2009/0043415 A1 | 2/2009 | Sun et al. | |
| 2012/0073989 A1 | 3/2012 | Wilke et al. | |
| 2015/0027385 A1* | 1/2015 | Von Der Osten-Sack | F02D 19/0621 123/3 |
| 2016/0283254 A1 | 9/2016 | Hill et al. | |
| 2017/0318803 A1* | 11/2017 | Gil | A01N 1/0247 |

FOREIGN PATENT DOCUMENTS

| | | |
|---|---|---|
| JP | 2005-083255 A | 3/2005 |
| JP | 2006-133069 A | 5/2006 |
| JP | 2008-096104 A | 4/2008 |
| JP | 2008-275416 A | 11/2008 |
| WO | 2012/177472 A2 | 12/2012 |

OTHER PUBLICATIONS

P.R. et al., "Monitoring of Fuel Supply in Power Plant Boilers using LabVIEW," International Journal of Advanced Research in Electrical, Electronics and Instrumentation Engineering, vol. 3, No. 9, pp. 12168-12172, (Sep. 2014).

Extended European Search Report and Opinion issued in connection with corresponding EP Application No. 16461578.3 dated Jul. 7, 2017.

Dinu.C et al., System and method for plant control based on fluid quality, GE co-pending U.S. Appl. No.15/385,438, filed Dec. 20, 2016.

Solar Turbines, A Caterpillar Company; Managing Liquid Fuel Cleanliness; 2008; ASTM D2880-03; X2 3.1.

Office Action issued in connection with corresponding EP Application No. 16461578.3 dated Jan. 28, 2019.

* cited by examiner

SYSTEM AND METHOD FOR PLANT FUEL QUALITY

BACKGROUND OF THE INVENTION

The subject matter disclosed herein relates to power plants, particularly systems and methods for improving reporting and control of the power plant based on fuel quality of the power plant.

BRIEF DESCRIPTION OF THE INVENTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

SUMMARY OF THE INVENTION

In a first embodiment, a plant-integrated measurement and monitoring system, includes: a first sampling port disposed in a first set of pipelines of a power plant that convey fuel from a fuel source to a dirty storage tank, the first sampling port providing a load sample of the fuel, the load sample representing the fuel provided by the fuel source prior to storage, processing, or both by the power plant. The system also includes a second sampling port disposed in a second set of pipelines downstream from a downstream component, the downstream component storing, processing, or storing and processing the fuel downstream from the dirty storage tank, and the second sampling port providing a post-downstream component sample of the fuel representative of fuel after processing, storage, or both of the fuel by the downstream component. The system also includes an automated analyzer device that: analyzes the load sample to determine quality attributes of the load sample; analyzes the post-downstream component to determine quality attributes of the post-downstream component; and provides the quality attributes of the load sample and the quality attributes of the post-downstream component to a distributed control system, enabling the distributed control system to identify anomalies in the fuel and attribute the anomalies as either an initial quality of the fuel as it is supplied by the fuel source or likely caused by the downstream component.

In a second embodiment, a method includes: receiving, from a first sampling port of a power plant, a load sample of fuel, the load sample representing the fuel provided by a fuel source prior to storage, processing, or both by the power plant; receiving, from a second sampling port of the power plant, a post-downstream component sample of the fuel representative of fuel after processing, storage, or both of the fuel by a downstream component; analyzing, via an automated analyzer device, the load sample to determine quality attributes of the load sample; analyzing, via the automated analyzer device, the post-downstream component sample to determine quality attributes of the post-downstream component; and providing, from the automated analyzer device, the quality attributes of the load sample and the quality attributes of the post-downstream component to a distributed control system, enabling the distributed control system to identify anomalies in the fuel and attribute the anomalies as either an initial quality of the fuel as it is supplied by the fuel source or likely caused by the downstream component.

In a third embodiment, a tangible, non-transitory, machine-readable medium, includes machine-readable instructions, to: analyze a load sample from a first location in a power plant near a fuel supply source to determine quality attributes of the load sample; analyze a post-downstream component sample from a second location downstream of a fuel storage, processing, or storage and processing component to determine quality attributes of the post-downstream component; and provide the quality attributes of the load sample and the quality attributes of the post-downstream component to a distributed control system, enabling the distributed control system to identify anomalies in the fuel and attribute the anomalies as either an initial quality of the fuel as it is supplied by the fuel source or likely caused by the downstream component.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
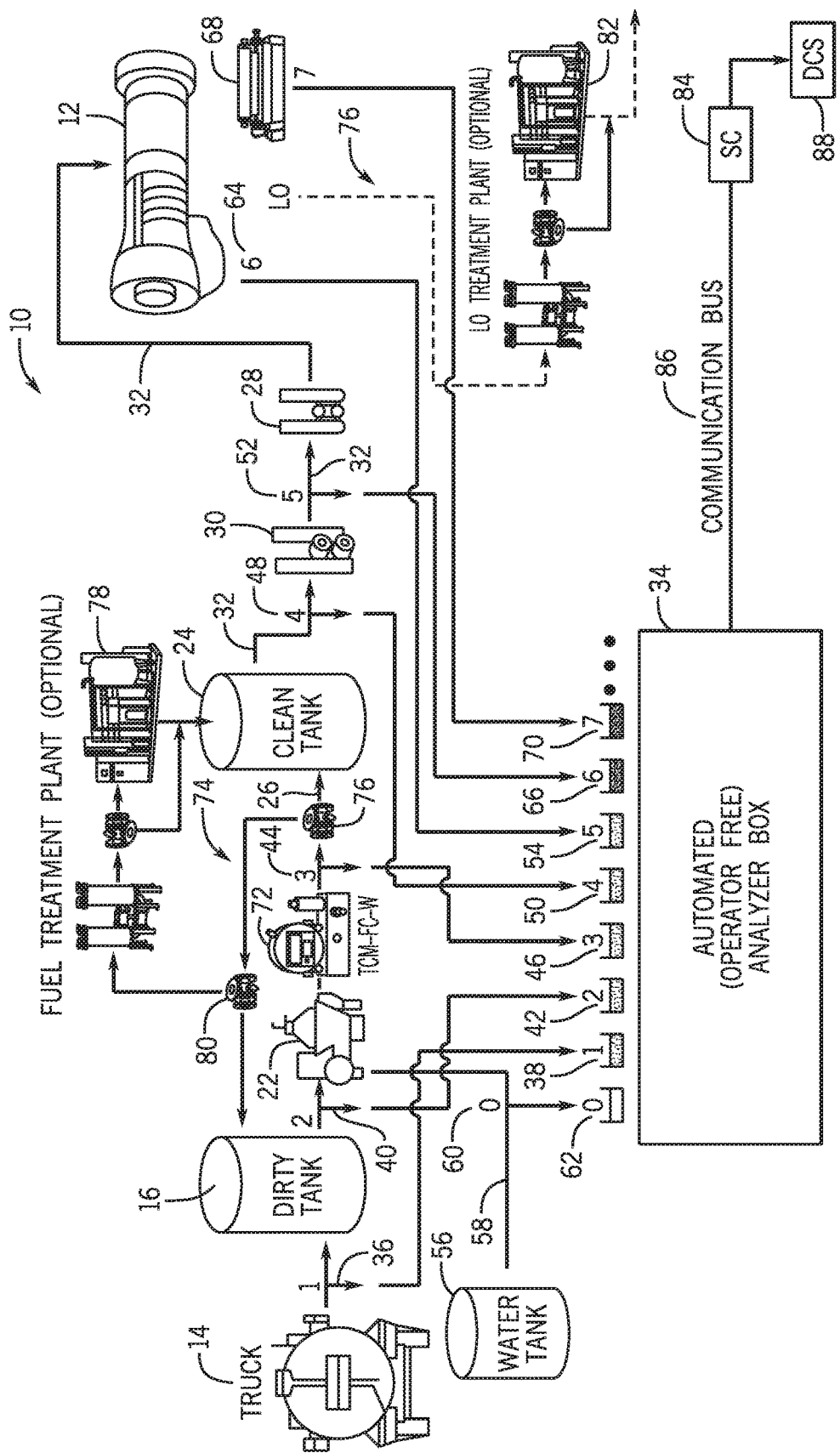
FIG. 1 is a block diagram of an embodiment of a fuel-fed power plant with fuel analysis circuitry, in accordance with an embodiment.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

The embodiments disclosed herein relate to a system and method for improving efficiency of a power plant, by reporting on and/or adjusting the operation of equipment (e.g., a condenser, turbine, etc.) in the power plant based in part on a near-real-time analysis of fuel, water, and/or oil characteristics of the power plant.

Power plant systems have developed across the globe. Equipment of these power plant systems may rely on fuel, water, oil and other fluids to facilitate the plant operations. As may be appreciated, certain quality standards of these fluids may be relied upon for proper functioning of the equipment. For example, certain fuel particulate levels, contaminant levels, etc. specifications may be provided by an equipment vendor, detailing particular thresholds for the fluids that will help ensure proper functioning of the equipment.

Unfortunately, given the vast number of fuel sources, fuel delivery systems, plant maintenance, global standards, etc., the quality of these fluids may vary significantly from time to time. For example, liquid fuel in certain areas may include high particulate, may include water and/or sediments, contaminants, and/or jelly deposits, which may degrade the quality of fuel for the power plant.

Typically, plant operations have assumed that incoming fuel meets the threshold specifications provided by a vendor. The plants may include monitoring that determines whether the equipment is functioning properly. However, this may only determine a problem in a reactionary manner, as the problems arise, due to fuel or other fluids not meeting these specifications. This may result in the Balance of Plant (BOP) system becoming fowled (e.g., contaminated), which can ultimately lead to subsequent engine damage, if proper reactive measures are not taken.

Such reactive measures can be quite costly. For example, when a pressure drop is found, indicating that a filter is clogged, there may be significant troubleshooting needed to determine an actual cause of the clogging. Further, it may be costly, both with time and money to remedy the issue, as the piping, etc. may need flushing.

The embodiments provided herein provide systems and methods for proactively alerting and/or acting upon an analysis of plant fluids (e.g., fuel, water, oil, etc.). For example, data logs, digital twin applications (e.g., digital 3D modeling of the power plant), plant maintenance scheduling, etc. may be updated based upon plant fluid analysis.

As discussed below, the power plant may include equipment, such as a compressor, a combustor, a gas turbine engine, a steam cycle, etc. The sensors may include flow rate sensors, acoustical wave sensors, temperature sensors, pressure sensors, humidity sensors, composition sensors, or any combination thereof. The controller may also receive data output by other sensors that are configured to measure operating conditions of other fluids of the power plant system, such as the compressor, the gas turbine, or other components. As discussed in more detail below, in some embodiments, fuel samples, water samples, lube oil samples, etc. may be obtained from particular areas in the power plant. These samples may be analyzed to provide pro-active reporting and/or control. For example, these samples may be analyzed to measure particular characteristics of the fluids, such as color, particulates (e.g., size and distribution) and contaminant identification (e.g., an identified particular type of contaminant, such as from the following list of contaminates, for example, Na, K, Li, V, Mg, Pb, Ni, Ca Mn, Cr, Si, Fe, Al, Cu, Zn).

For example, the controller may use the data output by the sensor to adjust the power usage of the condenser, as the load of the power plant changes. In some embodiments, fuel may be re-directed for additional treatment, diversion, etc. Further, operation of one or more of the components of the power plant may be altered based upon the outputted sensor data. For example, component operation may be reduced when increased contaminants are present in fuel. For example, the speed of fans within each condenser may be adjusted, the pitch of the fan blades may be adjusted, etc.

Turning now to the drawings, FIG. 1 is a block diagram of an embodiment of a power plant 10 having a gas turbine engine 12. The gas turbine engine 12 may be powered by fuel that is supplied by a fuel delivery system, such as the fuel truck 14. A dirty tank 16 may receive the fuel, via pipeline(s) 18. Further, the plant 10 may provide initial fuel treatment by supplying the fuel from pipeline(s) 20 to a centrifuge 22, where particulates and may be separated from the fuel. The treated fuel may be provided to a clean tank 24, via pipeline(s) 26 for storage until needed for use by the gas turbine engine 12. The fuel may be provided to the gas turbine engine 12 (e.g., after further downstream processing by filter 28 and/or other components 30), via pipeline(s) 32.

As will be discussed in more detail below, fluids of the plant 10 (e.g., the fuel, water, and lube oil) may be analyzed, at certain points of the power plant 10 operations, to determine certain characteristics (e.g., identify particular contaminates, particulate concentrations, etc.) of the fluids at these certain points. For example, in the embodiment of FIG. 1, an automated analyzer box 34 may receive component samples via one or more ports of the power plant 10. For example, when the plant 10 is equipped with supplementary filtering and/or conditioning equipment that can be engaged to correct fluid quality, additional sampling points may be provided to assess an effectiveness of these systems to help predict how long the plant 10 can operate before hardware distress may occur.

In one embodiment, Port1 36 may provide fuel samples from the pipeline(s) 18. Port1 36 may provide samples 38 of the initial fuel quality straight from the fuel supply source (e.g., the truck 14), prior to downstream processing and/or storage at the power plant 10. Accordingly, the automated analyzer box 34 may understand an initial fuel quality that is supplied to the power plant 10.

Additionally, Port2 40 may be provided at the pipeline(s) 20, supplying fuel from the dirty tank 16. Accordingly, these samples 42 may represent the state of the fuel after storage in the dirty tank 16. This may be useful in attributing fuel contamination to the dirty tank 16.

Port3 44 may be positioned after the centrifuge 22. The fuel sample 46 may provide an indication of the fuel quality after processing by the centrifuge 22, which may be useful to determine the effectiveness of the processing by the centrifuge 22.

Port4 48 may be placed after the clean tank 24. The fuel sample 50 may provide an indication of the fuel quality after storage in the clean tank 24. These fuel samples 50 may be useful to attribute contamination to the clean tank 24.

Port5 52 may be placed in the pipeline(s) 32 after additional equipment 30. The fuel samples 54 may be used to determine the fuel quality after the additional equipment 30 and/or before the filter 28.

As mentioned above, additional fluids may be analyzed. For example, the power plant may use water, which may be stored in the water tank 56. The pipeline(s) 58 may supply the water. Port6 60 of the gas turbine engine 12 may provide water samples 62 to the automated analyzer box 34. Further, lube oil samples may be provided to the automated analyzer box 34. For example, Port6 64 may provide samples 66 and additional equipment 68 that uses the lube oil may provide additional lube oil samples 70 to the automated analyzer box 34.

The automated analyzer box 34 and or additional sensors (e.g., the fuel quality sensor 72) may provide an indication of the quality of the fluids. When the quality is below a particular threshold branching pipeline(s), such as fuel treatment branching pipeline(s) 74 and/or lube oil treatment branching pipeline(s) 76 may divert the fluids for additional treatment. For example, when the fuel quality is below a threshold value, the valve 76 may be actuated to divert the fuel to the fuel treatment branching pipeline(s) 74 instead of storing the inadequate fuel in the clean tank 24.

The fuel treatment branching pipeline(s) 74 may divert the fuel to the fuel treatment plant 78 or send the fuel back to the dirty tank 16 for additional treatment by the centrifuge 22. The fuel quality sensor 72 and/or the automated analyzer box 34 may determine characteristics of the fuel and determine which option (e.g., fuel treatment plant 78 or additional centrifuge 22 processing). For example, small amounts of contamination may warrant additional centrifuge 22 treatment, while higher levels of contamination may warrant treatment at the fuel treatment plant 78. Accordingly, the valve 80 may be actuated accordingly, based upon the fuel quality analysis prior to the clean tank 24 (e.g., via samples 46).

Additionally, the automated analyzer box 34 may determine when the lube oil is below a threshold quality level. When below a threshold quality level, the lube oil may be diverted to a lube oil treatment plant 82 and/or alternative lube oil treatment equipment.

As will be discussed in more detail below, the automated analyzer box 34 may determine the containments and/or other characteristics of fluids of the power plant 10. The automated analyzer box 34 may be connected to a signal-conditioning device 84 via a communications bus 86. The signal conditioning device 84 may receive data indicative of the component quality and/or other characteristics via the communications bus 86. The signal-conditioning device 84 may convert this data into signals interpretable by a control system (e.g., distributed control system 88). Based upon the signals provided by the signal-conditioning device 84, the control system may provide alerts and/or control of equipment in the power plant 10.

Figure 2:
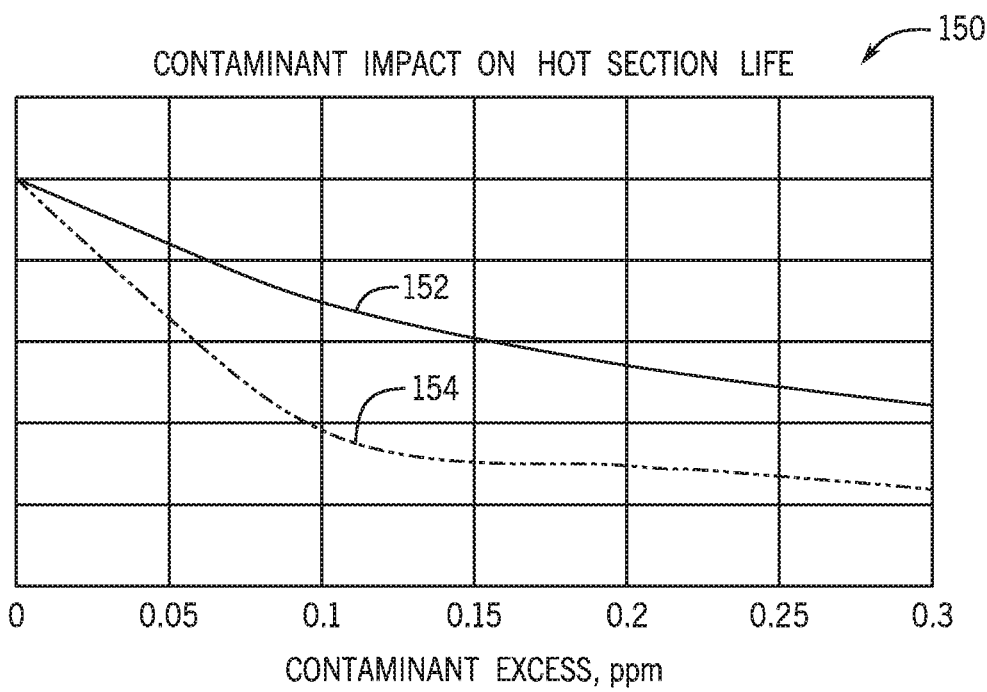
FIG. 2 is a line chart, illustrating a relationship between contaminant concentration of fuel and lifetime of fuel-fed components of the power plant.

FIG. 2 is a line chart 150, illustrating a relationship between contaminant concentration of fuel and lifetime of fuel-fed components of the power plant 10. The X-Axis provides an indication of a contaminant excess concentration in parts per million (ppm). The Y-Axis provides an indication of a life expectancy of the hot section (e.g., the combustor, turbine, afterburner, exhaust, etc.) of the gas turbine engine 12. The line 152 illustrates the effect of contaminant "A" and the line 154 illustrates the effect of contaminant "B". As illustrated by lines 152 and 154, as the contaminants increase, the life of the hot section equipment decreases. For example, at a 0 contaminant excess, the life of the hot section equipment is much higher than at a higher ppm content. Accordingly, as may be appreciated, the current techniques that analyze fluids throughout the power plant 10 may be useful in proactively notifying an operator and/or controlling operations in the plant 10, based upon contaminant levels.

Figure 3:
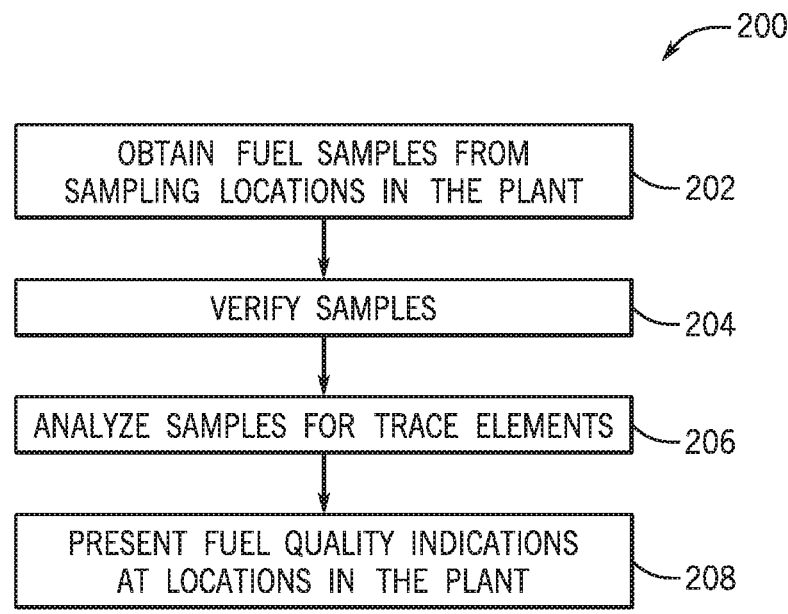
FIG. 3 is a flowchart illustrating a process for observing and analyzing power plant fuel used in the power plant of FIG. 1, in accordance with an embodiment.

FIG. 3 is a flowchart illustrating a process 200 for observing and analyzing power plant fuel used in the power plant of FIG. 1, in accordance with an embodiment. The process 200 begins by obtaining fuel samples (and/or other component samples) from Sampling locations in the plant 10 (block 202). For example, as mentioned above with regards to FIG. 1, samples may be provided to the automated analyzer box 34 from the ports (e.g., Port0 60, Port1 36, Port2 40, Port3 44, Port4 48, Port5 52, Port6 64, Port7 68).

Next, the samples may be verified (block 204). For example, optical techniques may be calibrated to measure liquid fuel opacity and/or color and/or may detect water content and/or particular loading. The system may further include automatic online particle sampling and binning devices.

The component samples may then be analyzed for trace elements (block 206). The samples are drawn from a pipe system designed to provide a continuous flow of fresh fluid at the analyzer location. As will be discussed in more detail below, the analyzer box 34, in one embodiment, is a robot (e.g., using rotating disk electrode atomic emission spectrometry) that receives the samples, executes analysis and provides a digitized signal encoding of the results of the analyses.

After analysis, present fuel quality indications at the various sampling locations in the plant 10 may be supplied for downstream altering and/or control (block 208). For example, a signal-conditioning device 84 may monitor for digital signals from the analyzer box 34. The signal-conditioning device 84 may sequence and condition the signals received from analyzer box 34 to provide control system discernable data to the distributed control system 88.

The process 200 may be implemented on a periodic basis. For example, the process 200 may be completed in near-real time, resulting in near-real time alerts and/or control. For example, in certain embodiments, the process 200 may be completed approximately every 5 minutes during power plant 10 operation.

Figure 4:
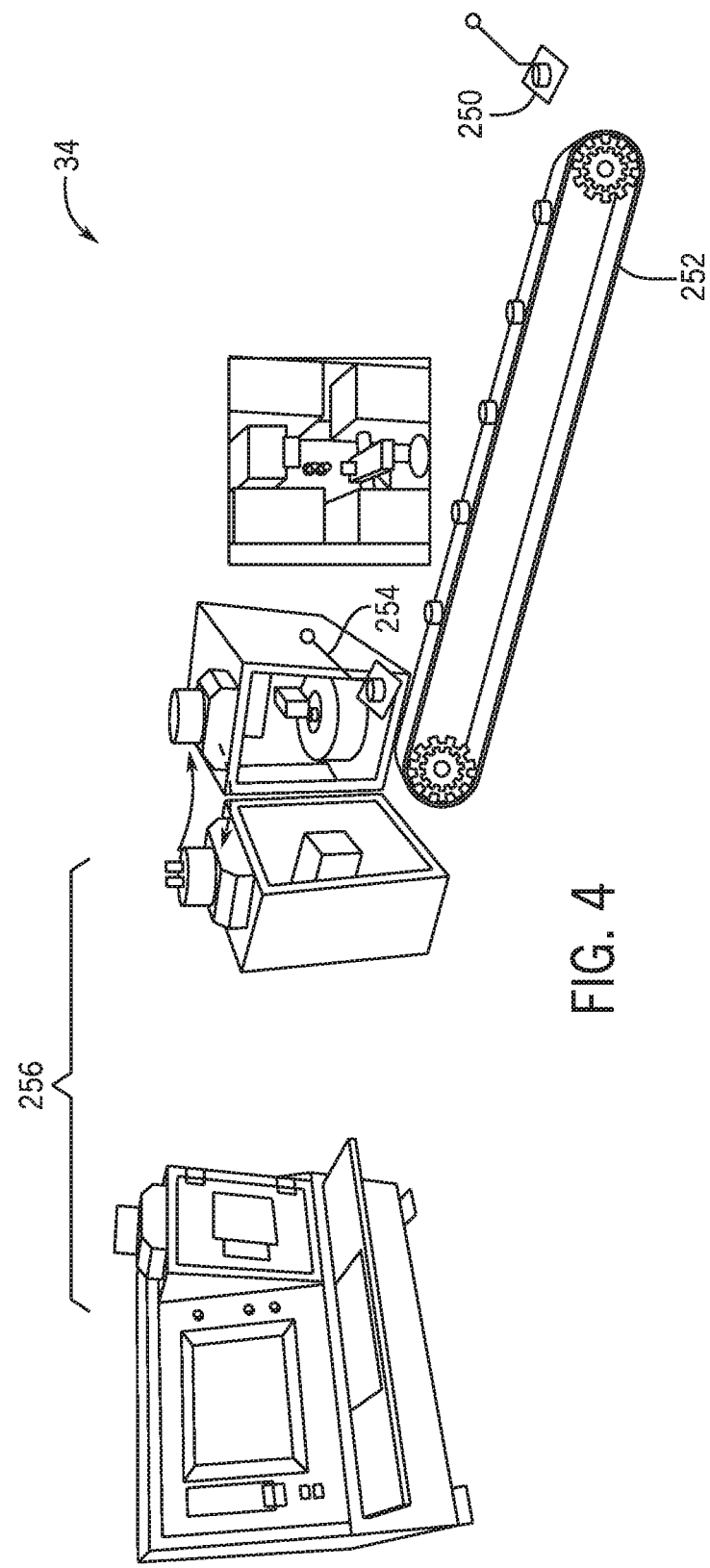
FIG. 4 is a block diagram illustrating a device for analyzing fuel, in accordance with an embodiment.

Turning now to a discussion of the automated analyzer box, FIG. 4 is a block diagram illustrating an embodiment of an automated analyzer device 34 for analyzing fuel, in accordance with an embodiment. As mentioned above with regard to FIG. 1, samples 250 may be prepared. The samples 250 may be positioned on a conveyor system 252. In some embodiments, some samples may be empty or contain a neutral liquid or a calibration standard to facilitate operation of the analyzer.

A robotic arm 254 may transfer the samples 250 (e.g., one at a time) to the analyzer 256. As mentioned above, the analyzer 256 may use rotating disk electrode technology to identify contaminate and/or particulate concentration levels. The analysis results may be provided from the analyzer 256 to a downstream component, such as a distributed control system 88.

Figure 5:
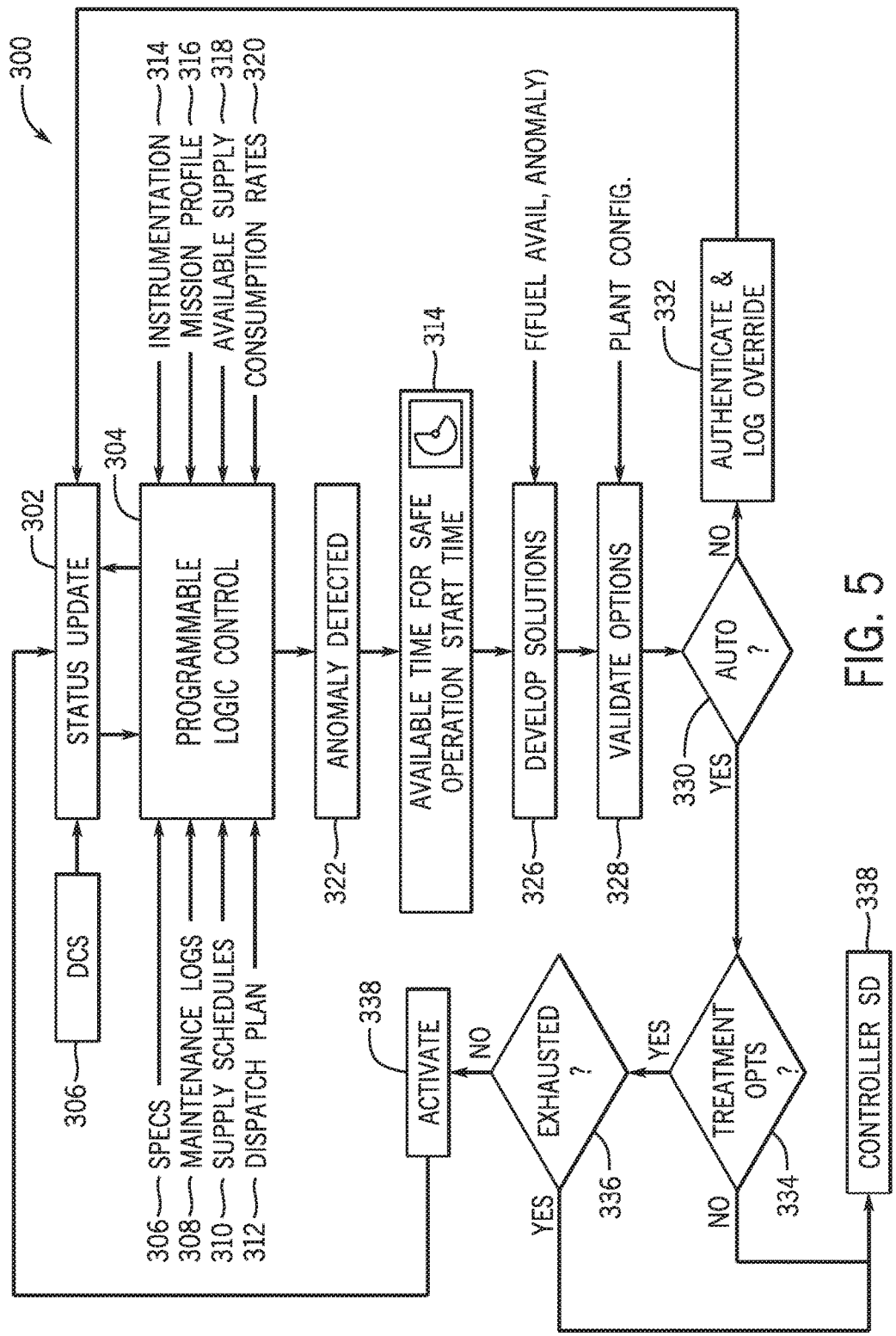
FIG. 5 is a flowchart, illustrating a process for electronic notification and control of a power plant based upon analyzed fuel quality, in accordance with an embodiment.

FIG. 5 is a flowchart, illustrating a process 300 for electronic notification and/or control of a power plant 10 based upon analyzed fuel, water, and/or lube oil quality, in accordance with an embodiment. As discussed with regard to FIG. 1, the distributed control system 88 may provide status updates 302 to a programmable logic controller (PLC) 304. The status updates 302 include an analysis of fluid samples taken from certain points in the power plant 10.

The PLC 304 may receive these status updates 302, along with other plant 10 information, such as equipment specifications 306, maintenance logs 308, supply schedules 310, dispatch plan 312, instrumentation 314, mission profile 316, available supply 318, consumption rates 320, etc. Based upon this received data, the PLC 304 may detect anomalies (e.g., non-conformity of the liquids as opposed to the plant requirements defined in the specifications 306) (block 322).

After detecting an anomaly, the PLC 304 may determine an amount of time remaining for safe operation, in light of the anomaly, and start a timer counting down an amount of time before operation of the plant 10 is to be altered (block 324). For example, relatively highly contaminated fuel may reduce a safe operation time for a gas turbine engine 12. Accordingly, the PLC 304 may determine a relatively low safe operation time. Additionally, the PLC 304 may trigger notifications (e.g., alarms, etc.) based upon the severity of the detected anomaly.

The PLC 304 (or other circuitry) may develop solutions for the anomaly based upon the available fuel supply 318, and the determined anomaly (block 326). For example, a Balance of Plant (BOP) capability and risk analysis (e.g., based upon the maintenance logs 308, instrumentation 314, specifications 306, mission profile 316, etc.) may be used to determine if the anomaly (e.g., the particular level of insufficient fuel quality) may be accepted and in what amount, such that plant 10 operations may continue. Supply vs. Demand, market conditions, and risk-based analyses can be implemented to maximize profit and/or minimize costs. Decision trees may take into account available redundant or optional filtration and/or conditioning systems to maximize run time and minimize impact on the equipment.

In some embodiments, a more complex analysis may detect if the identified anomaly is a direct result of low-quality fuel delivered to the plant 10 or due to malfunction in a particular portion of the plant BOP. For example, because the sampling locations are tracked with the samples, samples that indicate low-quality fuel can be attributed to particular portions of the plant 10. Plant instrumentation 314 and engine mission profile 316 may be integrated into the analysis to derive a comprehensive view of plant 10 health.

The PLC 304 (or other circuitry) may validate the options (block 328) to determine their viability with the current conditions. For example, detailed records including fuel, water, and lube oil condition along with operation history are used to enable Condition Based Maintenance. These records may establish remaining life of the components of the power plant 10 and risks involved in continued operations with the contaminated liquids. The potential solutions are ranked based upon their risk, plant configuration, and generation plans.

The PLC 304 (or other circuitry) may determine whether the control system of the power plant 10 is set to implement solution options automatically (decision block 330). If automatic implementation is not set, the plan may only be implemented after a user is authenticated and an override of current operations is selected by the user (block 332). Otherwise, if automatic implementation is set, the PLC 304 (or other circuitry) determines if treatment options for the anomaly are available (decision block 334). If there are treatment options, the PLC 304 (or other circuitry) determines whether the treatment options are exhausted (decision block 336). If there are not treatment options or the treatment options are exhausted, a controlled shutdown is performed by the end of the timer started in block 324 (block 338). However, when treatment options exist and have not been exhausted, the best of the available options (as determined during the validation option in block 328) is activated (block 338). Once these changes are implemented, the process 300 restarts, determining if the changes have enhanced the plant 10 operations and determining new safe operation times, etc.

Figure 6:
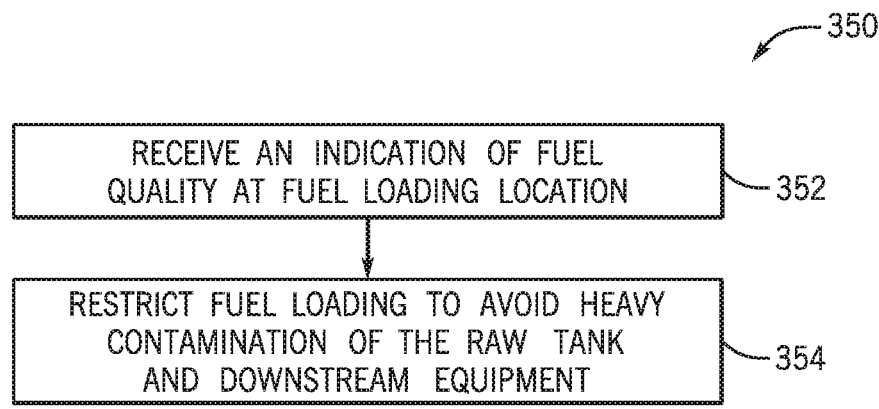
FIG. 6 is a flowchart illustrating a process for controlling fuel loading based upon fuel quality, in accordance with an embodiment.

As mentioned above, sometimes the initial fuel supply does not meet minimum requirements. FIG. 6 is a flowchart illustrating a process 350 for controlling fuel loading based upon an initial fuel quality, in accordance with an embodiment. First, an indication of fuel quality at the fuel loading location is received (block 352). For example, returning to FIG. 1, samples from the fuel analysis of Port1 36 may provide an indication of poor initial fuel quality. Based upon this information, the fuel loading may be restricted to avoid heavy contamination of the raw tank and downstream equipment. For example, valves may be actuated to cut access to the dirty tank 16. Additionally and/or alternatively, an alert of the poor fuel load may be provided via a human machine interface (HMI), enabling a power plant 10 operator to stop the fuel load manually.

Figure 7:
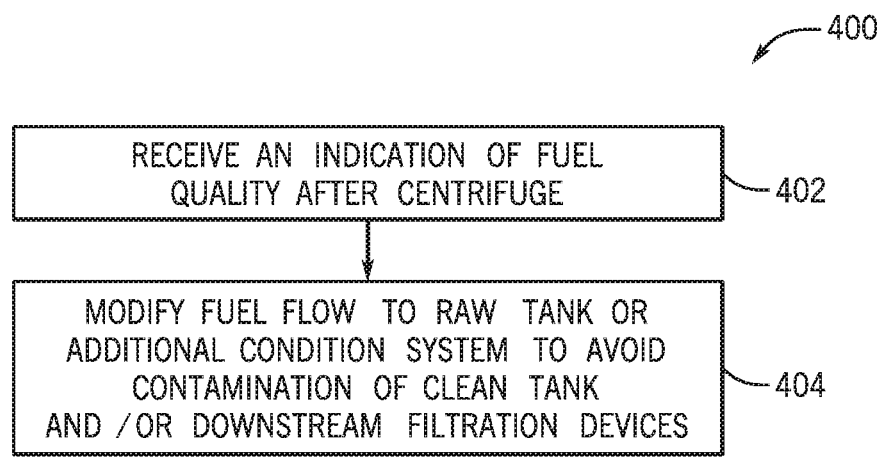
FIG. 7 is a flowchart illustrating a process for controlling the power plant based upon fuel quality, in accordance with an embodiment.

FIG. 7 is a flowchart illustrating a process 400 for controlling the power plant 10 based upon fuel quality, in accordance with an embodiment. First, an indication of the fuel quality after the centrifuge (e.g., centrifuge 22 of FIG. 1) (block 402). The fuel flow to the clean tank 24 may be removed and/or additional conditioning of the fuel may be implemented to avoid contamination of the clean tank and/or downstream filtration devices (block 404). For example, as mentioned above, regarding FIG. 1, the valve 76 may redirect fuel to valve 80, which may either direct the fuel to the fuel treatment plant 78 and/or back to the dirty tank 16, such that the fuel undergoes centrifuge 22 treatment again.

Various instructions, methods, and techniques described herein may be considered in the general context of computer-executable instructions, such as program modules, executed by one or more computers or other devices. Generally, program modules include routines, programs, objects, components, data structures, etc., for performing particular tasks or implementing particular abstract data types. These program modules and the like may be executed as native code or may be downloaded and executed, such as in a virtual machine or other just-in-time compilation execution environment. The functionality of the program modules may be combined or distributed as desired in various embodiments. An implementation of these modules and techniques may be stored on some form of computer-readable storage media.

Technical effects of the invention include a system and method for improving efficiency of a power plant, based in part on reporting the conditions of and/or adjusting the operation of equipment in the power plant based in part on an analyzed quality of the fuel at particular areas of the power plant. A controller uses the data output by fuel, water, and/or, oil analysis sensors to provide alerts and actions regarding the operation of the power plant. By providing alerts and/or actions based upon fuel, water, and/or oil analysis, pro-active actions may be performed, resulting in prolonged life-expectancy of the power plant equipment, a reduction in power-plant outages, etc.

Technical effects of the current system and methods include enabling condition based maintenance by providing advanced analytics to interpret current operational fluid qualities. Further, the current techniques provide mitigation plans, taking into account plant configuration and operation history and/or a risk/reward analysis. Accordingly, despite variability in quality of supplied liquid fuel and/or inadequate plant maintenance and/or inadequate operation of plant conditioning systems that cause varied fluid qualities, reliable operation and control of the plant 10 may be maintained, resulting in increased operational efficiencies with decreased downtime.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A plant-integrated measurement and monitoring system, comprising:
   a first sampling port disposed in a first set of pipelines that convey fuel from a fuel source to a dirty storage tank, the first sampling port configured to provide a load sample of the fuel, the load sample representing the fuel provided by the fuel source prior to storage, processing, or both;
   a second sampling port disposed in a second set of pipelines downstream from a downstream component, the downstream component configured to store, process, or store and process the fuel downstream from the dirty storage tank, and the second sampling port configured to provide a post-downstream component sample of the fuel representative of fuel after processing, storage, or both of the fuel by the downstream component;
   a first lube oil sampling port configured to provide a first lube oil sample; and
   an automated analyzer device configured to:
      analyze the load sample to determine quality attributes of the load sample;
      analyze the post-downstream component to determine quality attributes of the post-downstream component;
      analyze the first lube oil sample to determine quality attributes of the first lube oil sample; and
      provide the quality attributes of the load sample, the quality attributes of the post-downstream component, and the quality attributes of the first lube oil sample to a distributed control system, enabling the distributed control system to identify anomalies in the fuel and attribute the anomalies as either an initial quality of the fuel as it is supplied by the fuel source, or likely caused by the downstream component, or likely a result of lube oil.

2. The plant-integrated measurement and monitoring system of claim 1, wherein the downstream component comprises a centrifuge.

3. The plant-integrated measurement and monitoring system of claim 2, comprising:
   a third sampling port disposed between the dirty storage tank and the centrifuge, the third sampling port configured to provide a post-dirty storage tank sample of the fuel representative of fuel after storage in the dirty fuel tank.

4. The plant-integrated measurement and monitoring system of claim 3, wherein the automated analyzer device is configured to analyze the post-dirty storage tank sample to determine quality attributes of the post-dirty storage tank sample;
   provide the quality attributes of the post-dirty storage tank sample to the distributed control system, enabling the distributed control system to determine if the identified anomalies should be attributed to storage in the dirty storage tank.

5. The plant-integrated measurement and monitoring system of claim 1, wherein the first lube oil sampling port is disposed at a gas turbine engine.

6. The plant-integrated measurement and monitoring system of claim 1, comprising a first water sampling port configured to provide a first water sample to the automated analyzer device, wherein the automated analyzer device is configured to:
   analyze the first water sample to determine quality attributes of the first water sample; and
   provide the quality attributes of the first water sample to the distributed control system, enabling the distributed control system to determine if the identified anomalies are likely a result of water.

7. The plant-integrated measurement and monitoring system of claim 1, wherein the quality attributes of the load sample, the quality attributes of the post-downstream component sample, or both comprise: a particulate concentration, a water concentration, identification of contaminants, or any combination thereof.

8. The plant-integrated measurement and monitoring system of claim 1, wherein the automated analyzer device comprises:
   a conveyer system configured to provide samples from a sample preparation site to a liquid analyzer; and
   the liquid analyzer is configured to determine quality attributes of the samples.

9. The plant-integrated measurement and monitoring system of claim 8, wherein the automated analyzer device is configured to identify contaminants in samples when they exist, the contaminates comprising: Sodium (Na), Potassium (K), Lithium (Li), Vanadium (V), Magnesium (Mg), Lead (Pb), Nickel (Ni), Calcium (Ca), Manganese (Mn), Chromium (Cr), Silicon (Si), Iron (Fe), Aluminum (Al), Copper (Cu), and Zinc (Zn).

10. The plant-integrated measurement and monitoring system of claim 8, comprising:
    a signal-conditioning device configured to convert input signals into output signals interpretable by the distributed control system;
    wherein the automated analyzer device is configured to provide the quality attributes as the input signals to the signal-conditioning device via a communications bus.

11. The plant-integrated measurement and monitoring system of claim 8, wherein:
    the liquid analyzer is configured to determine quality attributes of the samples using a rotating disk electrode.

12. A method, comprising:
    receiving, from a first sampling port, a load sample of fuel, the load sample representing the fuel provided by a fuel source prior to storage, processing, or both;
    receiving, from a second sampling port, a post-downstream component sample of the fuel representative of fuel after processing, storage, or both of the fuel by a downstream component;
    analyzing, via an automated analyzer device, the load sample to determine quality attributes of the load sample;
    analyzing, via the automated analyzer device, the post-downstream component sample to determine quality attributes of the post-downstream component; and
    providing, from the automated analyzer device, the quality attributes of the load sample and the quality attributes of the post-downstream component to a distributed control system, enabling the distributed control system to:
    identify anomalies in the fuel; and attribute the anomalies as either an initial quality of the fuel as it is supplied by the fuel source or likely caused by the downstream component;

wherein the providing of the quality attributes of the load sample and the quality attributes of the post-downstream component to the distributed control system, comprises:

providing quality and location data regarding the fuel from the automated analyzer device via a communication bus to a signal-conditioning device;

converting the quality and location data to a DCS signal interpretable by the distributed control system; and providing the DCS signal to the distributed control system.

13. The method of claim 12, wherein analyzing the load sample to determine the quality attributes of the load sample comprises detecting a particulate concentration, detecting a water concentration, identifying contaminants, or any combination thereof of the load sample.

14. The method of claim 12, wherein analyzing the post-downstream component sample to determine the quality attributes of the post-downstream component sample comprises detecting a particulate concentration, a water concentration, identifying contaminants, or any combination thereof of the post-downstream sample.

15. The method of claim 12, comprising:

receiving at least one water sample and at least one lube oil sample from respective water ports and lube oil ports;

analyzing the at least one water sample and the at least one oil sample to determine quality attributes of the at least one water sample and the at least one oil sample; and providing the quality attributes of the at least one water sample and the at least one oil sample to the distributed control system, enabling the distributed control system to:

identify anomalies in power plant water, power plant lube oil, or both; and identify an associated location based upon a location where the at least one water sample and the at least one oil sample were sourced.

16. A tangible, non-transitory, machine-readable medium, comprising machine-readable instructions, configured to:

analyze a load sample from a first location near a fuel supply source to determine quality attributes of the load sample;

analyze a post-downstream component sample from a second location downstream of a fuel storage, processing, or storage and processing component to determine quality attributes of the post-downstream component;

analyze a lube oil sample from a gas turbine engine to determine quality attributes of the lube oil sample; and provide the quality attributes of the load sample, the quality attributes of the post-downstream component, and the quality attributes of the lube oil sample to a distributed control system, enabling the distributed control system to:

identify anomalies in the fuel;

attribute the anomalies as either an initial quality of the fuel as it is supplied by the fuel source or likely caused by the downstream component; and identify anomalies in lube oil.

17. The tangible, non-transitory, machine-readable medium of claim 16, comprising machine-readable instructions configured to:

analyze a water sample from a water tank to determine quality attributes of the water sample; and provide the quality attributes of the water sample to the distributed control system, enabling the distributed control system to identify anomalies in water.

18. A plant-integrated measurement and monitoring system, comprising:

a first sampling port disposed in a first set of pipelines that convey fuel from a fuel source to a dirty storage tank, the first sampling port configured to provide a load sample of the fuel, the load sample representing the fuel provided by the fuel source prior to storage, processing, or both;

a second sampling port disposed in a second set of pipelines downstream from a downstream component, the downstream component configured to store, process, or store and process the fuel downstream from the dirty storage tank, and the second sampling port configured to provide a post-downstream component sample of the fuel representative of fuel after processing, storage, or both of the fuel by the downstream component; and an automated analyzer device configured to:

analyze the load sample to determine quality attributes of the load sample;

analyze the post-downstream component to determine quality attributes of the post-downstream component; and provide the quality attributes of the load sample and the quality attributes of the post-downstream component to a distributed control system, enabling the distributed control system to identify anomalies in the fuel and attribute the anomalies as either an initial quality of the fuel as it is supplied by the fuel source or likely caused by the downstream component;

wherein the automated analyzer device comprises:

a conveyer system configured to provide samples from a sample preparation site to a liquid analyzer; and the liquid analyzer is configured to determine quality attributes of the samples.

19. A method, comprising:

receiving, from a first sampling port, a load sample of fuel, the load sample representing the fuel provided by a fuel source prior to storage, processing, or both;

receiving, from a second sampling port, a post-downstream component sample of the fuel representative of fuel after processing, storage, or both of the fuel by a downstream component;

receiving at least one water sample and at least one lube oil sample from respective water ports and lube oil ports;

analyzing, via an automated analyzer device, the load sample to determine quality attributes of the load sample;

analyzing, via the automated analyzer device, the post-downstream component sample to determine quality attributes of the post-downstream component;

analyzing the at least one water sample and the at least one oil sample to determine quality attributes of the at least one water sample and the at least one oil sample; and providing, from the automated analyzer device, the quality attributes of the load sample, the quality attributes of the post-downstream component, and the quality attributes of the at least one water sample and the at least one oil sample to a distributed control system, enabling the distributed control system to:

identify anomalies in the fuel;
attribute the anomalies as either an initial quality of the fuel as it is supplied by the fuel source or likely caused by the downstream component;
identify anomalies in power plant water, power plant lube oil, or both; and
identify an associated location based upon a location where the at least one water sample and the at least one oil sample were sourced.

* * * * *